(12) United States Patent
Van Der Meer et al.

(10) Patent No.: US 11,846,596 B2
(45) Date of Patent: Dec. 19, 2023

(54) MOBILE SYSTEM FOR CONTINUOUS, AUTOMATIC, ONLINE MONITORING OF WATER QUALITY AND PARTICLE SAMPLING IN A DRINKING WATER DISTRIBUTION NETWORK

(71) Applicant: OASEN N.V. [NL/NL], Gouda (NL)

(72) Inventors: Walterus Gijsbertus Joseph Van Der Meer, Gouda (NL); Gang Liu, Gouda (NL)

(73) Assignee: OASEN N.V. [NL/NL], Gouda (NL)

( * ) Notice: Subject to any disclaimer, the term of this patent is extended or adjusted under 35 U.S.C. 154(b) by 487 days.

(21) Appl. No.: 17/255,711

(22) PCT Filed: Jul. 1, 2019

(86) PCT No.: PCT/NL2019/050405
§ 371 (c)(1),
(2) Date: Dec. 23, 2020

(87) PCT Pub. No.: WO2020/005069
PCT Pub. Date: Jan. 2, 2020

(65) Prior Publication Data
US 2021/0270759 A1    Sep. 2, 2021

(30) Foreign Application Priority Data
Jun. 29, 2018  (NL) ................................ 2021210

(51) Int. Cl.
*G01N 27/06*    (2006.01)
*C02F 1/00*    (2023.01)
(Continued)

(52) U.S. Cl.
CPC ............ *G01N 27/06* (2013.01); *C02F 1/008* (2013.01); *G01N 1/2035* (2013.01); *G01N 33/18* (2013.01);
(Continued)

(58) Field of Classification Search
None
See application file for complete search history.

(56) References Cited

U.S. PATENT DOCUMENTS

| | | |
|---|---|---|
| 4,713,772 A | 12/1987 | Carlson |
| 2007/0007213 A1* | 1/2007 | MacPherson, Jr. ... C02F 1/5245 210/702 |

(Continued)

FOREIGN PATENT DOCUMENTS

| | | |
|---|---|---|
| DE | 102009048790 A1 | 7/2015 |
| KR | 20120034924 A | 4/2012 |

OTHER PUBLICATIONS

International Search Report dated Jan. 29, 2020 for PCT/NL2019/050405.

(Continued)

*Primary Examiner* — Jas A Sanghera
(74) *Attorney, Agent, or Firm* — Suiter Swantz pc llo

(57) ABSTRACT

The present invention relates to a mobile system for continuous, automatic, online monitoring of water quality and particle sampling in a drinking water distribution network, comprising: a mobile unit provided with means for supplying, from at least a selected one of the plurality of points in the drinking water distribution network, a corresponding, selected influent fluid sample stream; means for discharging a corresponding, selected effluent fluid sample stream; for each selected influent fluid sample stream, a respectively associated continuous monitor module.

16 Claims, 1 Drawing Sheet

(51) Int. Cl.
*G01N 1/20* (2006.01)
*G01N 33/18* (2006.01)
(52) U.S. Cl.
CPC .... *C02F 2209/008* (2013.01); *C02F 2209/02* (2013.01); *C02F 2209/03* (2013.01); *C02F 2209/05* (2013.01); *C02F 2209/06* (2013.01); *C02F 2209/40* (2013.01); *C02F 2307/14* (2013.01); *G01N 2001/205* (2013.01); *G01N 2001/2071* (2013.01)

(56) References Cited

U.S. PATENT DOCUMENTS

| | | | |
|---|---|---|---|
| 2007/0193932 A1* | 8/2007 | Nightingale | C02F 1/74 210/758 |
| 2011/0036775 A1* | 2/2011 | Tarquin | C02F 1/441 210/85 |
| 2014/0154138 A1 | 6/2014 | Lundgreen et al. | |
| 2016/0340204 A1 | 11/2016 | Chowdhury et al. | |
| 2017/0153217 A1 | 6/2017 | Johnston | |
| 2017/0336380 A1 | 11/2017 | McKeague et al. | |

OTHER PUBLICATIONS

Liu, G. et al., "Quantification and identification of Particle-associated bacteria in unchlorinated drinking water from three treatment plants by cultivation-independent methods", Elsevier, Water Research 47 (2013), pp. 3523-3433.

* cited by examiner

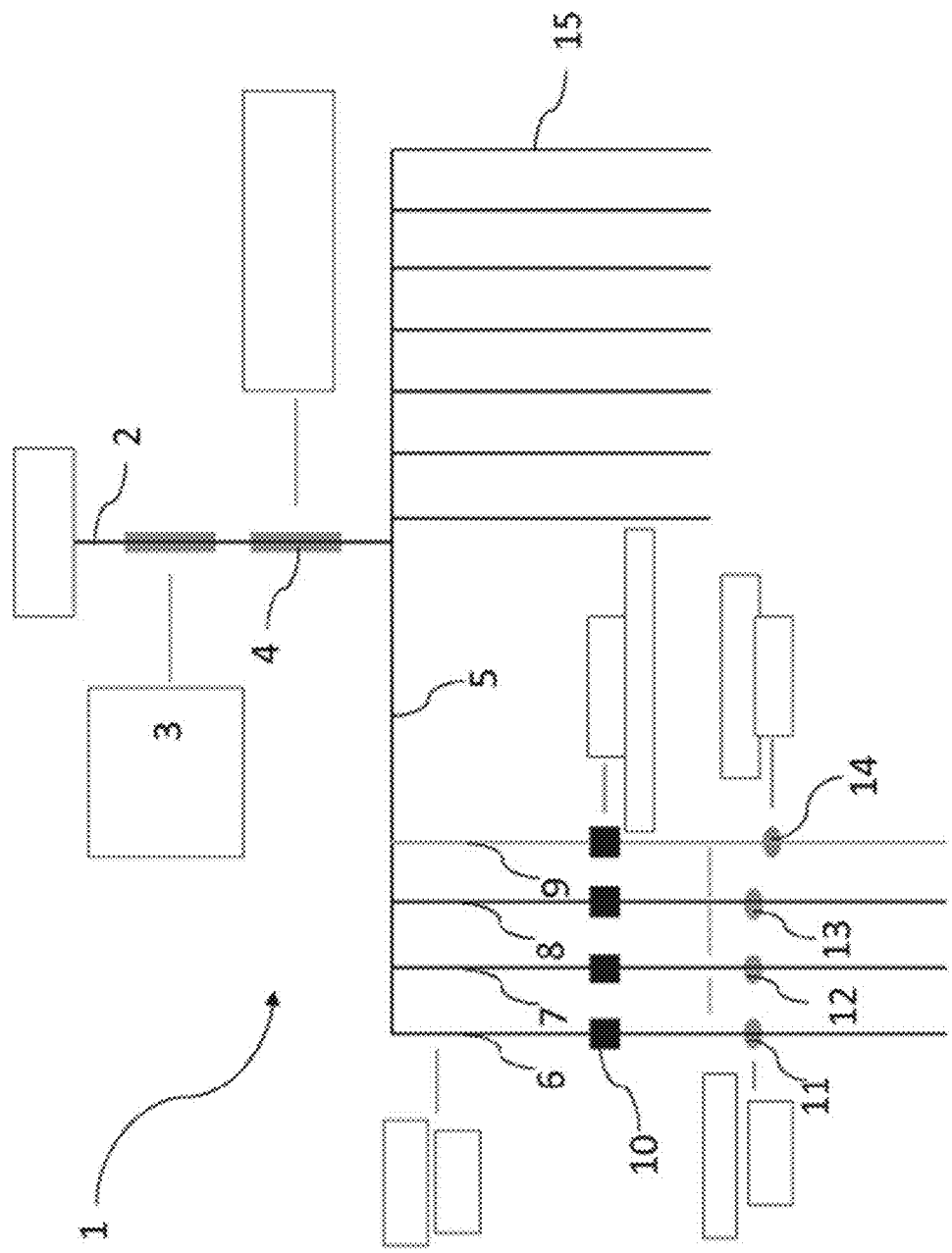

MOBILE SYSTEM FOR CONTINUOUS, AUTOMATIC, ONLINE MONITORING OF WATER QUALITY AND PARTICLE SAMPLING IN A DRINKING WATER DISTRIBUTION NETWORK

TECHNICAL FIELD AND BACKGROUND

The present invention relates to a mobile system for continuous, automatic, online monitoring of water quality and particle sampling in a drinking water distribution network. The present invention also relates to a method for continuous, automatic, online monitoring of water quality and particle sampling in a drinking water distribution network For many reasons, water quality, and the monitoring and testing of water, has become a very important undertaking in today's environment. More and more bodies of water are being monitored for quality on a regular basis. Further, water samples are being taken, analyzed and recorded for a greater number of locations within given bodies of water. The water samples are taken and analyzed in order to determine resident amounts of various chemicals and biological elements. These measurements are then logged into a database for subsequent planning purposes. As various actions are taken to purify or de-contaminate the water, sampling is again used to determine whether or not the water treatment plans are effective. Monitoring water quality can for example be carried out by using multi-sensor units called "multiprobes". The sensing devices or multiprobes are equipped with sensors to measure different water quality parameters or characteristics such as, inter alia, pH, dissolved oxygen, conductivity, salinity, temperature, turbidity, ammonia, nitrate, Oxidation Reduction Potential (ORP), and many others. The sensor devices may also include an electronic circuit board, analog and digital circuitry to control the operation of the sensors based upon a real time schedule.

To enhance water quality monitoring in a drinking water network, water sampling stations are installed at various points along the network's route. In the United States these sampling stations are typically positioned at street level, where they connect to a local water main, and are designed as enclosed, secured boxes containing a small sink and spigot to aid in sample collection. Collected samples are analyzed for bacteria, chlorine levels, pH, inorganic and organic pollutants, turbidity, odor, and many other water quality indicators. Using these stations, the New York City Department of Environmental Protection (DEP) collects more than 1,200 water samples per month from up to 546 locations.

KR20120034924 relates to a movable device for measuring water quality and collecting particle of a water supplying line. The movable device comprises an inlet for introducing the water sample into the movable device, in which device a water quality measurement unit is present and connected to one end of the inflow unit to measure the water quality of the sample water. The device also has a particle collecting part connected to another end of the inflow part to collect particles contained in the sample water. The device further contains a data storage unit for storing measured water quality values measured by the water quality measurement unit and the particle collecting unit. The flow of the water sample into the movable device is controlled by a manually operated valve.

US 2016/340204 relates to a method for monitoring quality of water flowing in a pipe, by diverting a flow of water from the pipe into a laser particle counter that continuously counts particles within a particle size interval in the diverted flow of water, diverting a flow of water from the pipe into a unit that separates the flow into a fraction of higher particulate concentration and a fraction of lower particulate concentration, and taking a sample of at least one of said fractions, and sending an alarm signal when a particle size exceeds a predetermined threshold during a predetermined length of time.

US 2017/336380 relates to a device for monitoring manual flushing of a hydrant, the device comprising an adapter constructed and proportioned to be attachable to an outlet of a water hydrant, an access port on the adapter, the access port being sized to take a sample of a stream of water flowing through the hydrant, a flexible hose attached to the access port, and an analyzer box containing a sensor adapted to sense a characteristic of water, the sensor being operatively connected to the flexible hose.

Systems for monitoring the characteristics of water sources is critical to many industries. Water sources that are of interest could be located in remote locations that are difficult to access by humans. Therefore, water monitoring is done by means of automated collection of samples by a sampler device. Automated remote sampling of water sources allows for sampling of water sources at varying times and locations. Traditionally, the remotely located samplers are delivered to their installed sites with a predetermined schedule for monitoring, for example with a preset sampling schedule of one sample every 12 hours.

A system for automatic, continuous online monitoring of water at any of a plurality of different points in water system is known from U.S. Pat. No. 4,713,772. This document is concerned with the control of impurities in a power plant steam cycle water and is recognized as being essential to the protection of a power plant's steam system against corrosion related failures. Plant chemistry monitoring is, for the most part, based on the on-line monitoring of only a few chemical characteristics, such as conductivity, pH, and dissolved oxygen concentration and many critical impurities which cause corrosion, such as chloride and sulfate, are checked only once or twice a day by laboratory analysis of grab samples. Grab sample data, since obtained only at long intervals, provides only an historical record of plant chemistry and is of little use in controlling the levels of corrosion causing impurities and thus in the prevention of corrosion related failures.

BRIEF SUMMARY

An aspect of the present invention is to provide a system for continuous, automatic, online monitoring of water quality in a drinking water distribution network, which system can be easily transported from one location to another location.

Another aspect of the present invention is to provide a system for continuous, automatic, online sampling of particles in a drinking water distribution network.

Another aspect of the present invention is to provide a system for continuous, automatic, online monitoring of water quality in a drinking water distribution network, which system can produce results over a specified time interval.

The present invention thus relates to a mobile system for continuous, automatic, online monitoring of water quality and particle sampling in a drinking water distribution network, comprising:

a mobile unit provided with means for supplying, from at least a selected one of the plurality of points in the drinking water distribution network, a corresponding, selected influent fluid sample stream;

means for discharging a corresponding, selected effluent fluid sample stream;

for each selected influent fluid sample stream, a respectively associated continuous monitor module comprising:

means for monitoring the temperature of the influent fluid sample stream and generating a corresponding temperature signal;

means for monitoring the flow rate of the influent fluid sample stream and generating a corresponding flow rate signal;

means for monitoring the pressure of the influent fluid sample stream and generating a corresponding pressure signal;

means for guiding said selected influent fluid sample stream to a bottle for collecting a water sample of the influent fluid sample stream;

means for guiding said selected influent fluid sample stream via a filter for collecting particles of the influent fluid sample stream; and measuring means responsive to at least the temperature, flow rate, pressure signals for determining a sample sequence thereof.

On basis of such a mobile system for continuous, automatic, online monitoring of water quality and particle sampling in a drinking water distribution network one or more objects of the present invention will be achieved. The mobile construction allows for an easy installation of the present monitoring system at any location. The mobile system includes for example a trailer that can be connected to a car or a small truck. This means that the mobile system is very flexible regarding the locations to be monitored. In addition, the present mobile system allows for the operation by only one person, as well. The present mobile system can be transported to different locations in the field if needed, which makes it mobile and possible to conduct experiments along the distribution. The present system further consists of a power supply, for example a battery, an inflow part, a sensor part, a sample part and a drainage part. In addition, the present mobile system may be equipped with a solar panel for electricity generation. The data, i.e. the signals mentioned here, is logged and uploaded to a server, for all measurements. The present system may further be provided with cooling means, for example a fridge part, the cooling means maintaining the samples at low temperature for quality reasons for microbiological analysis.

The battery is to provide energy to the whole system. There are two methods to charge the battery. Direct connection to the urban power network is the most efficient way but solar panel connections are possible as well. Furthermore, the trailer is preferably equipped with a petrol generator, which makes performing measurements flexible in the field. The battery supplies power to the sequencing appliances via a battery controller.

In an embodiment the continuous monitor module further comprises means for monitoring the electrical conductivity of the influent fluid sample stream and generating a corresponding electrical conductivity signal.

In an embodiment the continuous monitor module further comprises means for monitoring the pressure of the effluent fluid sample stream and generating a corresponding pressure signal. On basis of the pressure signal from both the effluent fluid sample stream and the influent sample stream one can determine the pressure drop over the mobile system. The pressure drop over the mobile system is an indication of the particle load in the water.

In order to prevent an influence of the outdoor conditions on the measurements the continuous monitor module is preferably placed in a temperature controlled environment, for example an environment having a standard temperature and relative humidity level.

In an embodiment the means for guiding the selected influent fluid sample stream further comprise a main influent pipe, the main influent pipe being connected to at least one secondary pipe, wherein the at least one secondary pipe is provided with a filter for collecting particles.

In an embodiment the means for guiding the selected influent fluid sample stream further comprise a main influent pipe, the main influent pipe being connected to at least one secondary pipe, wherein the at least one secondary pipe is provided with at least one bottle, said bottle being preferably sealed and isolated from surrounding air, said bottle being used for sampling water.

In an embodiment the main influent pipe is connected to several secondary pipes, each secondary pipe has a specific function, i.e. for collecting particles or sampling water.

In an embodiment the continuous monitor module further comprises means for switching the main influent pipe to at least another secondary pipe, wherein the means for switching are controlled via a time programmed sequence. Such a construction allows for a continuous, reproducible automatic sample program.

In an embodiment one or more signals chosen from the group of temperature, flow rate, influent pressure, effluent pressure and electrical conductivity, are sent to a monitor unit, wherein the monitor unit transmits the signals as received to an electronic data system. Such a data system may be connected to a wireless system, for example the internet. The data thus produced can be used for further analysis of the water quality.

The present system for continuous, automatic, online monitoring of water quality and particle sampling in a drinking water distribution network allows for a continuous operation to achieve 24-hour sampling. According to an embodiment of the present system one day is divided in eight periods with each period lasting for three hours. For each period, a water source to be analyzed is directed from a main influent pipe to a plurality of secondary pipelines, for example three secondary pipelines. Every secondary pipe is provided with means for collecting particles, for example a filter housing containing a filter. In an embodiment one of three secondary pipes is connected to means for collecting a water sample, for example a bottle for collecting the liquid samples. Such a bottle is well sealed and isolated from the air. When the bottle is filled with the water sample, all water will be pushed to the filter to be filtrated. After a certain time period, for example three hours, the flow direction of the main influent pipe will be changed automatically, and another three filters start to run. On basis of the above, a number of twenty four filters (solids samples) and eight liquid samples can be collected. The physiochemical and biological characteristics of the samples, both liquid (bottle) and solid (filter), can be examined in a lab. The result of the present system is that the characteristics of the solid particles (filter) are analyzed and thus any changes of water quality can be monitored and studied.

The water to be analyzed flows into the present system from an influent connector fixed on the bottom of the trailer which can be connected to the distribution system directly. The entrance valve is set after the connector, acting as the switch as well as the flow adjuster. In a specific embodiment there are twenty four pipes which guide the water to be analyzed to different filters and achieve measurements at different time periods.

The present system is preferably controlled by PLC (programmable logic controller). Different types of sensors measure the pressure of influent and effluent, average flow rate, pH, temperature and electrical conductivities. The effluent pressure sensor is connected to the effluent pipe and all other sensors are fixed on the main inflow pipe. All values are monitored at a specific time interval which can be read off on an interface screen.

In an embodiment the monitor module is placed in a temperature controlled area for maintaining a proper temperature to guarantee a constant quality of the samples taken. In an embodiment twenty four pipes are present and each line is equipped with a filter holder and a valve. Among these twenty four pipes, only eight pipes are connected to one bottle separately for liquid samples.

The present invention furthermore relates to a method for continuous, automatic, online monitoring of water quality and particle sampling in a drinking water distribution network, comprising:
  i) providing a drinking water distribution network.
  ii) obtaining an influent sample stream from said drinking water distribution network,
  iii) sending said influent sample stream to a plurality of branch lines, in which branch lines automatic controllable valves are present, said plurality of branch are provided with filters for collecting parts or bottles for sampling water,
  iv) operating said automatic controllable valves in such a way that according to a specific sample regime each branch line is individually provided with said influent sample stream, and
  v) collecting filter samples and water samples according to said specific sample regime.

In an embodiment the influent sample stream is measured for one or more parameters, chosen from the group of temperature, pH, pressure, flow rate, conductivity and flow cytometer (counting cell number), or a combination thereof.

In an embodiment step iv) includes the provision of a specific branch line with the influent sample stream during a specific time interval and, after that specific time interval, another branch line is provided with the influent sample stream during a specific time interval. In such an embodiment the automatic controllable valves will send the influent sample stream to a specific branch line during a specific time interval. After that period another branch line is connected to the influent sample stream. Thus several branch lines are connected to the influent sample stream in a specific sequence, i.e. one after another. For example, one branch line is used for collecting a water sample whereas the other one is used for collecting a particle sample. In an embodiment it is thus possible to operate some of the branch lines together, i.e. an embodiment for collecting a water sample and a particle sample at the same time but via different branch lines. Each branch line has a specific function, namely collecting particles, i.e. a filter, or collecting a water sample, i.e. a bottle.

In an embodiment the operation of the automatic controllable valves takes place via a PLC (programmable logic controller).

In an embodiment the data obtained from the present method is logged and uploaded to a server, for all measurements.

BRIEF DESCRIPTION OF THE DRAWING

FIG. 1 shows a schematic diagram of a mobile system for continuous, automatic, online monitoring of water quality and particle sampling in a drinking water distribution network.

The present invention will be discussed with reference to the sole FIGURE.

DETAILED DESCRIPTION

The FIGURE shows an example of a mobile system 1 for continuous, automatic, online monitoring of water quality and particle sampling in a drinking water distribution network. Influent fluid sample stream 2, i.e. a supply line for water to be analysed, is sent to a plurality of branch lines 6, 7, 8, 9 and 15. The flow of water in stream 2 is analysed for a number of parameters, such as temperature, pH, and pressure, conductivity, via one or more sensors 3. In this embodiment an additional sensor 4, i.e. an online flow cytometer (counting cell number), is present in stream 4 as well. The mobile system 1 shown here refers to a sample cycle of for example 0-3 hrs. The flow of water through line 5 is sent to a plurality of branch lines 6, 7, 8, and 9. In these branch lines 6, 7, 8, and 9 automatic valves 10 are present. Automatic valves 10 are connected to a PLC box (not shown here). The branch lines 6, 7, 8 are provided with filters 11, 12 and 13 for collecting particles, respectively. Branch line 9 is provided with a bottle for sampling water. In operational mode water to be analysed is passed from an inlet point via sensors 3, 4, line 5 to one of the branch lines 6, 7, 8, and 9. In case the automatic valves in branch lines 6, 7, and 8 are closed and the automatic valve in branch line 9 is open, a water sample will be taken by filling water bottle 14. After filing water bottle 14 with water, the automatic valve in branch line 9 will be closed and one or more of the automatic valves in branch lines 6, 7, and 8 will be opened. The water flow coming from line 5 will then be passed through one or more of filters 11, 12 and 13 for collecting particles. In an embodiment the filters 11, 12 and 13 will be operated according to a specific time program. For example, filter 11 will be operated in a period of 0-1 hrs, filter 12 will be operated in a period of 1-2 hrs and filter 13 will be operated in a period of 2-3 hrs. Thus each filter 11, 12 and 13 corresponds to a certain time range of the sample regime. In this example another group of branch lines 15 will be operated in the following periods, for example in a period of 3-6 hrs, in a period of 6-9 hrs, in a period of 9-12 hrs etc. This means that for every period several filter samples and a water sample will be collected. In another embodiment filters 11, 12, 13 can be operated from 0-3 h together, that triplicate filter/particle samples can be collected. Line 14, in this embodiment may take a water sample for 0-3 h.

Thus, in the main supply line there are multiple sensors for measuring temperature, pH, conductivity, pressure, and an online flow cytometer measuring cell numbers in the water. In total, there are preferably thirty lines, four lines will run as a group for every three hours, each controlled by an auto-valve for open and close. Within those four lines, three lines are used for filtration to collect suspended particles by a filter placed in the filter holder (for example 1.2 μm glass fiber filters are being used), the other line is connected to sampling bottle for collecting water samples. Collected particle and water samples are analyzed on physiochemical and microbiological parameters.

The samples, i.e. solids and liquids, can be analysed on physiochemical and microbiological parameters (ATP, elements, Aeromonas, D N A et al.). For obtaining reliable liquid and solid samples it is preferred to store all filters and sampling bottles in a temperature controlled environment, for example a fridge. In terms of readability a PLC box, additional valves, pumps, control panel have not been described here. In another embodiment a different sample regime may be applied, for example filters 11, 12, 13 can be operated from 0-3 h together resulting in the collection of triplicate filter/particle samples. In such an embodiment branch line 14 may take a water sample for 0-3 h. The period of taking samples is not critical here. This means that taking samples may take place during a sample program of for example 0-2 h, 2-4 h, 4-6 h, or 0-1 h, 1-2 h, 2-3 h etc.

It is to be noted that the embodiment discussed here is not limited to a specific number of sensors, branch lines, automatic valves, filters etc. The embodiment describes the present mobile system 1 for continuous, automatic, online monitoring of water quality and particle sampling in a drinking water distribution network only for illustrative purposes.

The invention claimed is:

1. A mobile system for continuous, automatic, online monitoring of water quality and particle sampling in a drinking water distribution network, comprising:
a mobile unit provided with
means for supplying, from at least a selected one of a plurality of points in the drinking water distribution network, a corresponding, selected influent fluid sample stream;
means for discharging a corresponding, selected effluent fluid sample stream;
for each selected influent fluid sample stream, a respectively associated continuous monitor module comprising:
means for monitoring the temperature of the influent fluid sample stream and generating a corresponding temperature signal;
means for monitoring the flow rate of the influent fluid sample stream and generating a corresponding flow rate signal;
means for monitoring the pressure of the influent fluid sample stream and generating a corresponding pressure signal;
means for guiding said selected influent fluid sample stream to a bottle for collecting a water sample of the influent fluid sample stream;
means for guiding said selected influent fluid sample stream via a filter for collecting particles of the influent fluid sample stream; and
measuring means responsive to at least the temperature, flow rate, pressure signals for determining a sample sequence thereof.

2. The mobile system according to claim 1, wherein said continuous monitor module further comprises means for monitoring the electrical conductivity of the influent fluid sample stream and generating a corresponding electrical conductivity signal.

3. The mobile system according to claim 1, wherein said continuous monitor module further comprises means for monitoring the pressure of the effluent fluid sample stream and generating a corresponding pressure signal.

4. The mobile system according to claim 1, wherein said continuous monitor module is placed in a temperature controlled environment.

5. The mobile system according to claim 1, wherein said means for guiding said selected influent fluid sample stream further comprise a main influent pipe, said main influent pipe being connected to at least one secondary pipe, wherein said at least one secondary pipe is provided with said filter for collecting particles.

6. The mobile system according to claim 5, wherein thirty secondary pipes are present, wherein four of the secondary pipes are configured run as a group, for every three hours, each controlled by an auto-valve for open and close.

7. The mobile system according to claim 6, wherein a group of four of the secondary pipes comprises three secondary pipes for collecting particles and one secondary pipe for sampling water.

8. The mobile system according to claim 1, wherein said means for guiding said selected influent fluid sample stream further comprise a main influent pipe, said main influent pipe being connected to at least one secondary pipe, wherein said at least one secondary pipe is provided with at least one bottle, said bottle being sealed and isolated from surrounding air, said bottle being used for sampling water.

9. The mobile system according to claim 1, wherein said continuous monitor module further comprises means for switching said main influent pipe to at least another secondary pipe, wherein said means for switching are controlled via a time programmed sequence.

10. The mobile system according to claim 1, wherein one or more signals chosen from the group of temperature, flow rate, influent pressure, effluent pressure and electrical conductivity, are sent to a monitor unit.

11. The mobile system according to claim 10, wherein said monitor unit transmits the signals as received to an electronic data system.

12. A method for continuous, automatic, online monitoring of water quality and particle sampling in a drinking water distribution network, comprising:
i) providing a drinking water distribution network including means for guiding an influent sample stream to a bottle for collecting a water sample of the influent sample stream, means for guiding said influent sample stream via a filter for collecting particles of the influent sample stream, and measuring means responsive to at least a temperature, a flow rate, and pressure signals for determining a sample sequence,
ii) obtaining the influent sample stream from said drinking water distribution network,
iii) sending said influent sample stream to a plurality of branch lines, via the means for guiding, in which branch lines include automatic controllable valves, said plurality of branch lines further including filters for collecting parts or bottles for sampling water,
iv) operating said automatic controllable valves according to a predefined sample regime such that each branch line is individually provided with said influent sample stream, and
v) collecting filter samples and water samples according to said predefined sample regime.

13. The method according to claim 12, wherein said influent sample stream is measured for one or more parameters, chosen from the group of temperature, pH, pressure, flow rate, and conductivity, or a combination thereof.

14. The method according to claim 12, wherein step iv) includes providing a specific branch line with said influent sample stream during a specific time interval and, after said specific time interval, providing another branch line with said influent sample stream during a further specific time interval.

15. The method according to claim 12, wherein operating said automatic controllable valves is controlled by a programmable logic controller (PLC).

16. The method according to claim 12, wherein data obtained from the method is logged and uploaded to a server.

\* \* \* \* \*